United States Patent [19]

Kappas et al.

[11] Patent Number: 4,657,902
[45] Date of Patent: Apr. 14, 1987

[54] THERAPEUTIC USE OF TIN MESOPORPHYRIN

[75] Inventors: Attallah Kappas; George S. Drummond, both of New York, N.Y.

[73] Assignee: The Rockefeller University, New York, N.Y.

[21] Appl. No.: 715,515

[22] Filed: Mar. 25, 1985

[51] Int. Cl.$^4$ ..................... A61K 31/40; C07D 209/94
[52] U.S. Cl. ..................................... 514/185; 540/145
[58] Field of Search ................... 260/245.91; 514/185; 540/145

[56] References Cited

U.S. PATENT DOCUMENTS 3,579,533  5/1971  Yalman ........................... 260/245.91
3,687,863  8/1972  Wacher ....................... 260/245.91 X

FOREIGN PATENT DOCUMENTS

83/00287  2/1983  PCT Int'l Appl. .

OTHER PUBLICATIONS

Fisher et al, Z. Physical Chem., vol. 154 (1926) pp. 39–63.
Hill et al, Biochem. J., vol. 20 (1926) pp. 1326–1339.
Shul'ga et al, Chemical Abstracts, vol. 76 (1972) 71737a.

Primary Examiner—Richard L. Raymond
Attorney, Agent, or Firm—Wyatt, Gerber, Shoup, Scobey and Badie

[57] ABSTRACT

Use of the novel compound tin mesoporphyrin and compositions containing it to inhibit heme metabolism in mammals, to control the rate of tryptophan metabolism in mammals, and to increase the rate at which heme is excreted by mammals.

11 Claims, 4 Drawing Figures

Figure 3:
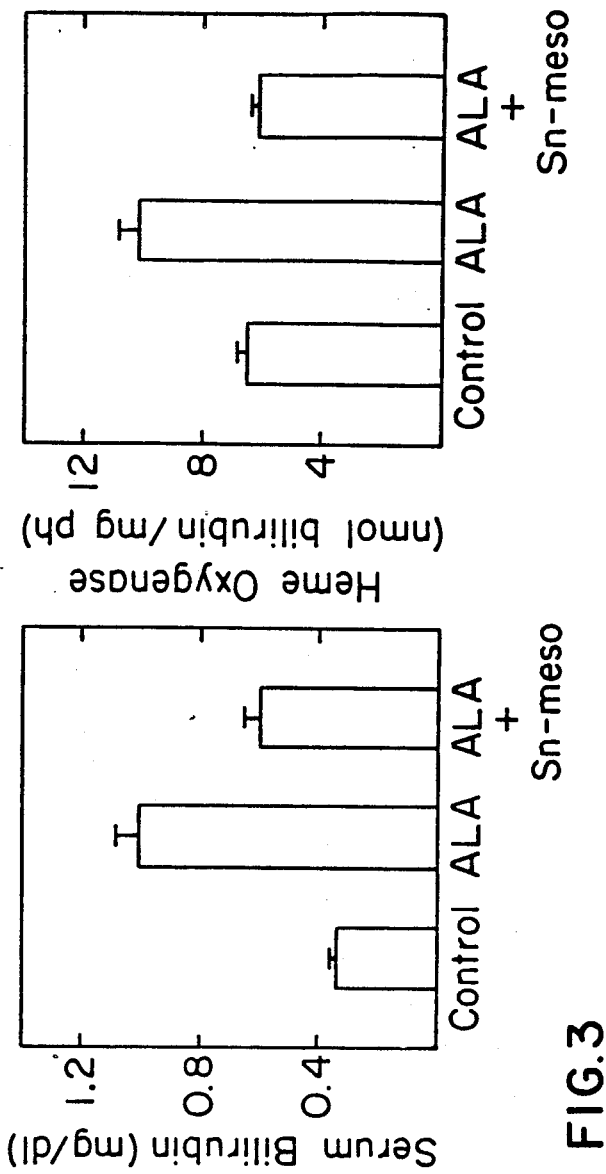

FIG.3 Effect of Sn-mesoporphyrin on ALA Induced Hyperbilirubinemia and Hepatic Heme Oxygenase Activity in 7day old Neonates

THERAPEUTIC USE OF TIN MESOPORPHYRIN

BACKGROUND OF THE INVENTION

This invention relates to the compound tin mesoporphyrin, to therapeutically useful compositions containing it, and to the use of the compound and the compositions in treating various metabolic afflictions of mammals, particularly humans.

Heme is a red pigment comprised of four subunits called pyrroles; these subunits are chemically joined to form a single large tetrapyrrole (porphyrin) ring structure. A metal atom is chelated at the center of this porphyrin: in higher organisms this metal is iron and the porphyrin ring structure is called protoporphyrin IX. In physiological systems heme is bound to certain proteins; these hemeproteins bind oxygen at the site of the metal atom or they function as components of membrane bound electron transport systems. Cellular respiration, energy generation and chemical oxidations are dependent on these hemeproteins.

In mammals and other vertebrates heme is oxidatively degraded by heme oxygenase to form the open chain tetrapyrrole biliverdin. In mammals biliverdin is reduced to bilirubin by biliverdin reductase. In liver bilirubin is converted to the mono- and di-glucuronide conjugates by the hepatic glucuronyl transferase system prior to its excretion.

Bilirubin is a toxic compound, but normally this toxicity is not manifest since bilirubin is rapidly bound to plasma proteins, transported to liver, conjugated and excreted. However in the newborn high undesirable concentrations of bilirubin exist in serum and may produce neurotoxicity. The intractable neurological syndrome known as "kernicterus" is the most severe manifestation of bilirubin toxicity.

The basis of this neonatal hyperbilirubinemia lies in a number of factors, mainly the rapid hemolysis of fetal erythrocytes after birth and a developmental immaturity of the hepatic conjugating system which normally facilitates the excretion of bilirubin via the bile. The levels of heme oxygenase, the rate limiting enzyme in the catabolism of heme to bilirubin are also markedly elevated at this time resulting in high rates of production of this bile pigment. Current methodologies for suppressing severe neonatal jaundice include a. stimulation of the hepatic conjugating system for bilirubin by drugs, e.g. phenobarbital, b. partial exchange transfusion, and c. phototherapy. None of these methods is fully satisfactory since there are as yet many unanswered questions with respect to their safety. In addition all these methods are directed towards the disposition of bilirubin once it has been formed in the heme degradative sequence—a complex process to undertake at best.

Elevated levels of bilirubin also often appear in the serum of individuals with diseases such as congenital anemias, thalassemia and sickle cell anemias as well as various forms of liver disease. The concentration of bilirubin in the serum of such individuals rarely reaches the high levels found in neonates. It does, however, attain levels which can be toxic and should be controlled.

It is therefore desirable to have available methods and materials to inhibit the catabolism of heme in order to prevent the accumulation of bilirubin in serum.

Copending and commonly assigned U.S. patent application Ser. No. 684,169, now abandoned, describes the use of tin protoporphyrin IX in the treatment of elevated levels of bilirubin in neonates and adults.

Maintenance of a proper equilibrium or balance of tissue heme content is essential to the normal physiological functioning of cells. When this equilibrium is disturbed by any condition characterized by excess heme—as exemplified by the circumstances listed above—it would be clinically valuable to have a pharmacological mechanism for restoring the equilibrium state of heme in cells by facilitating the excretion of the excess amount of heme from the body.

In association with but independent of the conditions described above, excess iron also accumulates in the body and this accumulation of the metal over time can produce deleterious and even lethal consequences for the host. This excess of iron may derive from several sources; e.g. cooking methods (iron pots) or directly via the diet (e.g., iron-overload induced cutaneous porphyrin), from excess therapeutic administration of the metal in an attempt to vigorously treat unresponsive anemias; from hypertransfusions to which certain patients with blood disorders are subject; idiopathically from the disorders collectively known as "hemachromatosis"; from certain industrial exposures; but the most common causes of excess iron deposition in tissues, and the resultant pathologic consequences which derive thereof, are a consequence of common congenital hemolytic anemias such as sickle cell disease, the various forms of thalassemia, G-6-PD deficiency, hereditary spherocytosis and the like. In these disorders, a greatly shortened red cell life span results in continuous large depositions of iron in tissues to an extent exceeding the capacity of the body to re-utilize the metal. Thus tissue concentrations of iron rise to very high, toxic levels and lead to impairment of vital organ functions manifest for example by cardiomyopathy, pancreatic insufficiency (diabetes) and generalized endocrine failure.

There is no physiological mechanism for excreting this excess of iron and the only generally available therapeutic modality for this purpose is a pharmacological agent known as desferrioxamine. This agent is not specific for iron however and chelates other metals as well; it must in order to be reasonably effective be given intramuscularly and causes substantial local inflammation at the site of injection. Further, original suggestions that it was non-toxic have proved incorrect and a large number of toxic reactions in treated patients have now been reported to occur after its use, including hypotension and allergic reactions.

Sn- protoporphyrin (Sn-PP) as described in copending and commonly assigned U.S. patent application Ser. No. 691,459 manifests the extremely advantageous property of greatly enhancing the biliary excretion of iron into the intestinal contents where the metal is eliminated. Sn-PP acts in this additional fashion by blocking the binding of heme to heme oxygenase, thus preventing the release of iron which normally occurs in the process of heme catabolism and allowing one atom of iron to be excreted into the intestine with every molecule of uncatabolized heme.

Tryptophan is an essential amino acid which has profound effects on a number of metabolic pathways in the whole animal, including man, particularly in the nervous system. Tryptophan is metabolized principally in the liver. Tryptophan which is not metabolized in the liver accumulates in the plasma and in the brain. Brain levels of tryptophan are dependent on plasma levels of the amino acid which in turn are regulated by liver tryptophan pyrrolase. Tryptophan in the brain is metabolized by a different route than in the liver. One of the principal metabolic products of tryptophan in the brain is 5-hydroxytryptamine, or serotonin. The concentrations of tryptophan and serotonin in the brain are closely regulated in humans. Increased concentration of these products are associated with hepatic encephalopathy and migraine headaches. Encephalopathy is a known affliction characterized by degenerative changes in the brain cells leading to confused states and other abnormal behaviour patterns as well as convulsions, stupor and coma. Decreased concentrations of these products have been implicated in narcolepsy, depression and myoclonic disorders characterized by uncontrolled jerky movements.

Tryptophan pyrrolase is an enzyme which occurs in the liver of humans. It catalyzes the oxidative cleavage of tryptophan to N-formylkynurenine and is the first and rate-limiting enzyme in the catabolism of tryptophan in the liver. The active holoenzyme is normally about 50% saturated with heme, but fluctuations in the availability of cellular heme produce rapid changes in the enzyme activity by converting the inactive, heme-free apoenzyme to the active heme containing holoenzyme.

More specifically, and as described in copending and commonly assigned U.S. patent application Ser. No. 691,460, an increase in the amount of heme in the liver as can be produced by parenteral administration of Sn-PP as a result of the ability of this compound to block the catabolism of heme causes increased saturation of tryptophan pyrrolase as the active form of the enzyme. The increased activity of the enzyme resulting from its increased saturation with heme causes an increased rate of tryptophan metabolism in the liver. As a result there is less spill-over of intact tryptophan into the plasma and, ultimately, less accumulation of tryptophan and serotin in the brain.

THE INVENTION

It has now been discovered that the compound Sn(tin)-mesoporphyrin (SnMP) can be employed in the treatment of mammals including humans in need of such treatment to decrease the rate of heme metabolism, to increase the rate at which heme is excreted and to control the rate of tryptophan metabolism in the liver.

SnMP may be prepared by treating mesoporphyrin IX with excess stannous chloride under acid conditions, preferably in an inert atmosphere. The mesoporphyrin IX may be obtained by reduction of protoporphyrin IX with hydrogen on palladium.

In the preparation, a molar excess, e.g. 3 molar excess of stannous chloride is dissolved in acetic acid under a nitrogen atmosphere. While continuing to flush with nitrogen, free mesoporphyrin IX is added and the mixture is stirred for 24 to 48 hours at a slightly elevated temperature which does not exceed 50° C. The optimum period of time for the reaction may be determined by following the reaction with a hand spectroscope. The 4 line spectrum of mesoporphyrin IX changes to a 2 line spectrum when the incorporation of the tin into the mesoporhyrin is complete. The mixture is then allowed to stand for about 10 hours during which period the SnMP crystallizes and is recovered by filtration through Whatman No. 1 filter paper. It is washed with glacial acetic acid.

The product is purified after air drying by stirring with 6N HCl followed by filtering and washing with additional 6N HCl. The final step is to wash with 0.1 N HCl and dry in vacuo.

Figure 1:
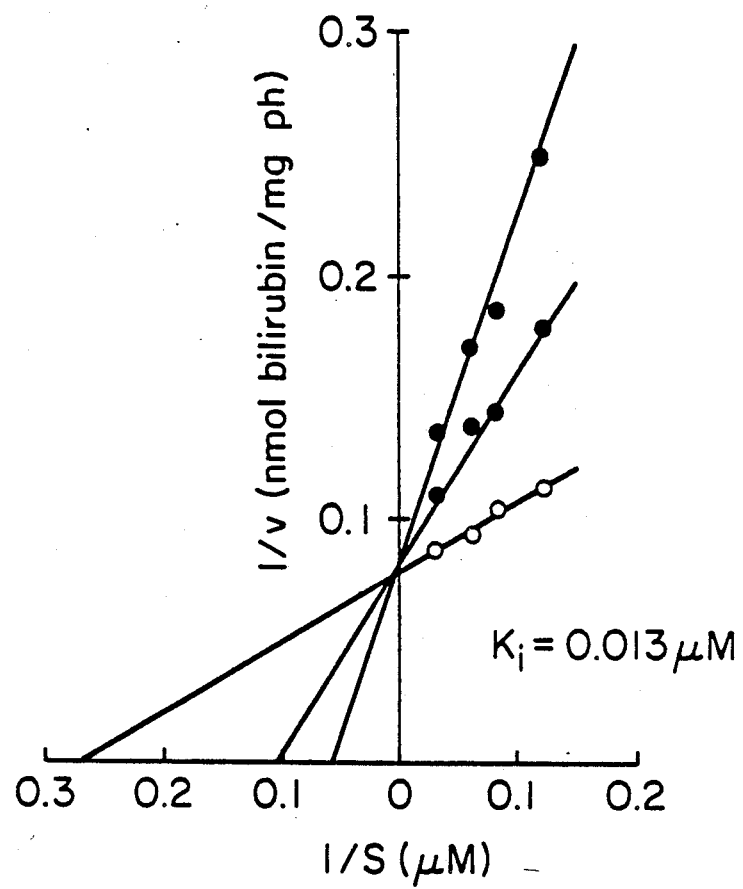

In an initial in vitro study, SnMP was shown to competitively inhibit the activity of heme oxygenase. In this study, the addition of 0.025 and 0.05 $\mu$M of SnMP to rat spleen - heme oxygenase incubation mixtures resulted in a marked competitive inhibition of hem oxygenase activity, and a significant increase in Km, the rate constant for degradation of heme by heme oxygenase to bile pigment. The decrease was from the normal 3.64 $\mu$M to values of 11.11 $\mu$M and 18.18 $\mu$M respectively at concentrations of 0.025 M and 0.05 $\mu$M, respectively. The inhibition constant $K_i$ for the inhibition of the conversion of heme to bilirubin by heme oxygenase was found to be 0.013 $\mu$M. The data are shown in FIG. 1.

This study established the in vitro ability of SnMP to inhibit the productin of bilirubin. It was just about as effective in this regard as SnPP. It was however, unexpectedly discovered that in vivo SnMP was about 5-10 times as effective as SnPP in lowering plasma bilirubin.

Figure 2:
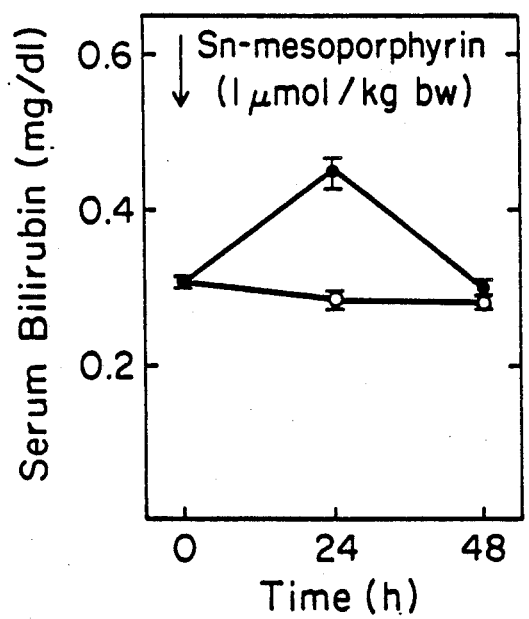

This latter fact was established in a study in which SnMP was administered once at birth to newborn rats by subcutaneous injection in a volume of 0.1 ml. To prepare the solution for parenteral administration, SnMP was taken up in a small volume of 0.2 N sodium hydroxide, adjusted to pH 7.4 with 1N hydrochloric acid and made up to final volume with 0.9% sodium chloride. The solution as prepared and used contained a final SnMP concentration of 1 $\mu$mol/kg body weight in each 0.1 ml injection volume. Control neonates received 0.1 ml of 0.9% sodium chloride at birth. Groups of neonates ($\mu$ 20 animals) were sacrificed at the times indicated in FIG. 2 Total bilirubin in serum was estimated by the method of Roth, *Clin. Chem. Acta*, 17, 487-492, 1967. SnMP administration entirely prevented the immediate and significant increase in the levels of serum bilirubin that occurred in the control animals 24 hours after birth as shown in FIG. 2.

The efficacy of SnMP for controlling hyperbilirubinemia was also examined in a model of experimental postantal hyperbilirubinemia in the rat utilizing the heme precursor 2-aminolevulinic acid (ALA) to produce jaundice 7 days after birth (Drummond & Kappas, *J. Clin. Invest.*, 74, 142-149, 1984). AlA (50 $\mu$mol/100g body weight) administered to suckling 7 day old neonates at 0,4 and 8 hours produced an approximately 3 fold increase in serum bilirubin levels 24 hours after the initial injection (FIG. 3). A single dose of SnMP (1 $\mu$mol/kg body weight) administered at 0 time substantially diminished the marked increase in serum bilirubin produced by ALA (FIG. 3). In addition SnMP administration prevented the increase in hepatic heme oxygenase activity associated with ALA administration (FIG. 3). Heme oxygenase was assayed as earlier described (*J. Biol. Chem.*, 253, 2321-2326, 1978).

It is therefore apparent that SnMP can effectively decrease the rate of heme catabolism to the toxic bile pigment, bilirubin. The studies described herein represent the first use of SnMP to suppress hyperbilirubinemia in the newborn animal and they reveal this compound to be 5-10 times more potent in suppressing neonatal jaundice than SnPP.

With newborn mammals, the therapeutic compositions of this invention will be administered promptly after birth at a dosage of from 00.5 to 2.5 um/kg of body weight. While appreciable variations from this range can be tolerated without unacceptable adverse effects, this range appears to be the most practical. Any of the usual parenteral routes may be employed. Normally, one injection will suffice to maintain the bilirubin concentration at a desired low level until the infant reaches the age where the metabolism of heme is in balance. It is preferred, however, to monitor the serum bilirubin concentration and to utilize a booster dose, if necessary.

Figure 4:
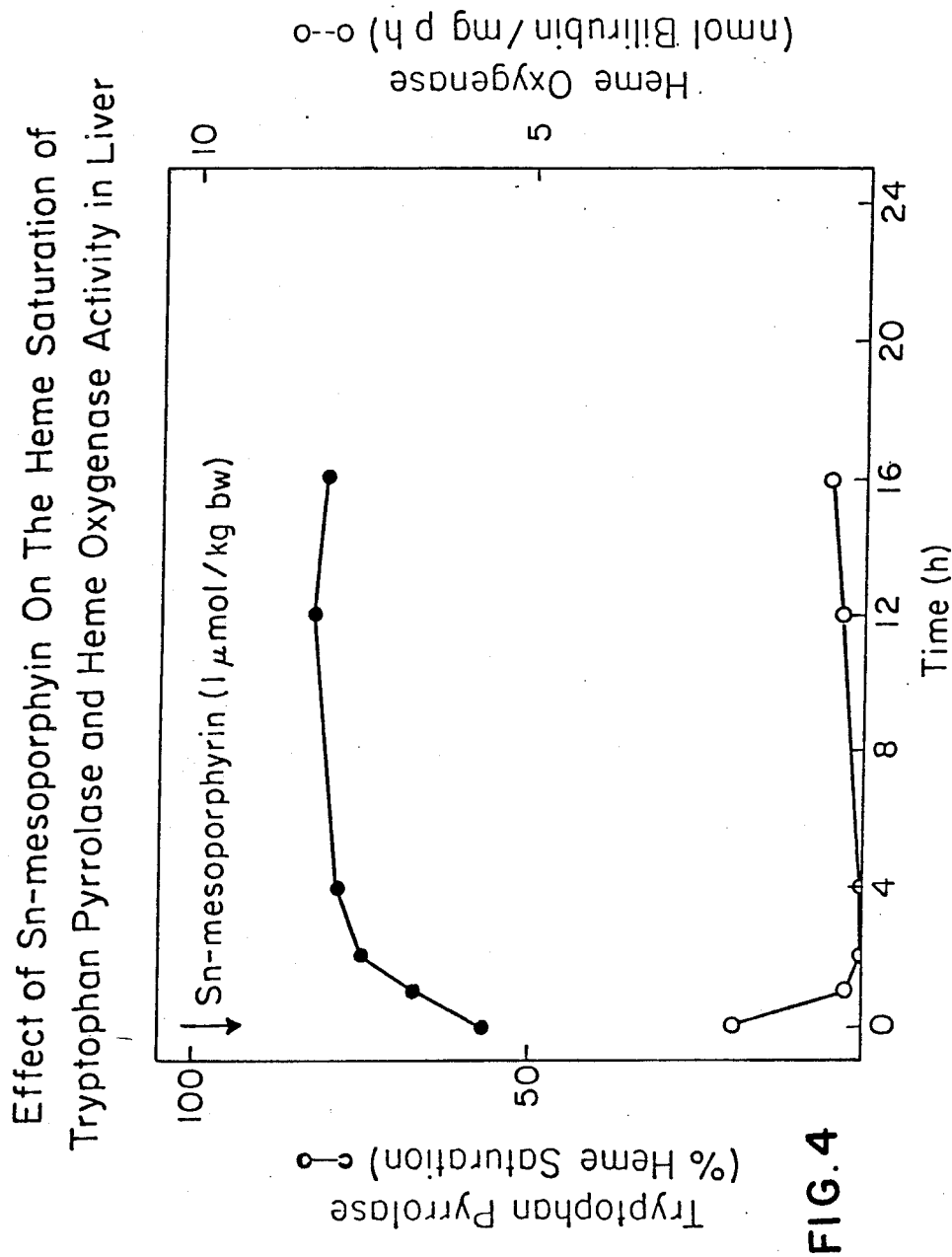

With adults afflicted with sickle cell anemia or another condition resulting in increased bilirubin concentration, the dosage unit is normally smaller since in all but the most acute situations, the bilirubin concentration is not as high as in neonates. The standard dosage with adults will normally be from about 2 to 5 mg/kg of body weight. FIG. 4 shows the changes in liver tryptophan pyrrolase activity resulting, from parenteral administration of SnMP to rats. In this study SnMP was administered subcutaneously at a dosage level of 1 $\mu$mol/kg of body weight to male Sprague-Dawley rats (180-200g). Control animals received an equivalent volume of aqueous isotonic saline. Tissue preparation of liver fractions for enzymic assays were conducted as described by Drummond and Kappas. Proc. Natl. Acad. Sci. USA. 78:6466-6470 (1981). Tryptophan pyrrolase activity was determined both in the absence (holoenzyme) and the presence (total enzyme) of added heme (2 m). The latter enzyme activity was calculated from the linear phase of kynurenine formation. The percent heme saturation for tryptophan pyrrolase was expressed as the ratio of holoenzyme to total enzyme ($\times$100). Each data point in the figure represents the mean value of determinations in 3 to 6 animals.

It will be noted that the injection of the selected dose of SnMP caused a marked and rapid increase in the percent heme saturation and resulting tryptophan pyrrolase activity, reaching approximately 80% saturation in two hours.

It is interesting to note that the initial high activity is maintained for a more extended period of time than that initial level is maintained with SnPP.

The results shown in FIG. 4 clearly establish the ability of the SnMP to control tryptophan pyrrolase activity and thereby control the rate of tryptophan metabolism in the liver.

A therapeutic dose of SnMP for use in the control of tryptophan metabolism is the same as for that employed to control heme metabolism; but the effect is longer lasting.

It has been observed that when heme is administered alone to animals such as rats, a large output of biliary bilirubin (mono- and diglucuronide forms) occurs, with a slight output of excess heme. When SnMP is administered with the heme to these animals, the bilirubin peak will decline, indicating an inhibited conversion of heme to the bile pigment, while the output of heme will increase.

Administration of SnMP to bile duct cannulated rats will result in an increase in output of biliary iron. It is therefore clear that the administration of SnMP to mammals increases the biliary excretion of excess heme and thus of its contained iron atom as well. They make it clear also that the excess heme which accumulates when the rate of bilirubin production is decreased by the administration of SnMP is excreted in the bile and not stored in tissues. More particularly, they make it clear that the administration of SnMP to mammals suffering acute or chronic excess of heme or iron will increase the rate at which such heme or iron will be excreted into the intestinal contents.

The dosage range for SnMP employed for increasing the rate at which heme is excreted is about the same as that employed for the aforementioned purposes.

Therapeutic compositions of this invention will be prepared by the usual procedures employed for such purposes. The usual pharmaceutical carriers for parenteral administration may be used such as aqueous media made isotonic by the addition of sodium chloride, glucose or other standard solutes. Typically the compositions will be buffered, for example with a phosphate buffer to a pH of about 7 to 8, preferably 7.4 to 7.5. The concentration of SnMP in the composition will be from 1 to 250 $\mu$g/liter, so that they can be formed into dosage unit forms adequate to provide a dosage of from 0.01 to 2.5 $\mu$g/kg body weight. Accordingly, the dosage units will normally contain from 2 mg/ml to 25 mg/ml of solution.

What is claimed is:

1. A pharmaceutical composition for parenteral administration comprising tin mesoporphyrin and pharmaceutically acceptable carrier.

2. A pharmaceutical composition in dosage unit form for parenteral administration comprising tin mesoporphyrin at a concentration of 1-250 $\mu$m/liter in a pharmaceutically acceptable carrier.

3. A pharmaceutical composition useful for decreasing the rate of metabolism of heme in mammals in need of such decreased rate comprising a buffered isotonic aqueous saline solution containing an amount of tin mesoporphyrin which is effective to decrease said rate.

4. A pharmaceutical composition useful for decreasing the rate of metabolism of heme in mammals in need of such decreased rate comprising a buffered isotonic aqueous glucose solution containing an amount of tin mesoporphyrin which is effective to decrease said rate.

5. A pharmaceutical composition of claims 1, 3 or 4 in dosage unit form.

6. A method of decreasing the rate of metabolism of heme in a mammal in need of such decreased rate which comprises parenteral administration of an amount of the tin mesoporphyrin which is sufficient to effect such decrease.

7. A method as in claim 6 wherein the mammal is a human.

8. A method as in claim 6 wherein the tin mesoporphyrin is parenterally administered in the form of a buffered isotonic aqueous saline solution.

9. A method as in claim 8 wherein the mammal is a human.

10. A method as in claim 6 wherein the tin mesoporphyrin is parenterally administered in the form of a buffered isotonic aqueous glucose solution.

11. A method as in claim 10 wherein the mammal is a human.

* * * * *